(12) United States Patent
Serrano Mollar et al.

(10) Patent No.: US 9,610,305 B2
(45) Date of Patent: Apr. 4, 2017

(54) METHOD FOR USING TYPE II PNEUMOCYTES IN PULMONARY FIBROSIS

(75) Inventors: Ana Maria Serrano Mollar, Barcelona (ES); Daniel Closa Autet, Barcelona (ES); Jose Oriol Bulbena Moreu, Barcelona (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 1472 days.

(21) Appl. No.: 12/095,028

(22) PCT Filed: Nov. 27, 2006

(86) PCT No.: PCT/ES2006/070182
§ 371 (c)(1),
(2), (4) Date: Sep. 19, 2008

(87) PCT Pub. No.: WO2007/060278
PCT Pub. Date: May 31, 2007

(65) Prior Publication Data
US 2009/0220467 A1  Sep. 3, 2009

(51) Int. Cl.
*A61K 35/42* (2015.01)

(52) U.S. Cl.
CPC .................................... *A61K 35/42* (2013.01)

(58) Field of Classification Search
CPC ...................................................... A61K 35/42
See application file for complete search history.

(56) References Cited

U.S. PATENT DOCUMENTS

2002/0182732 A1   12/2002   Borok et al.
2008/0274088 A1*  11/2008   Panoskaltsis-Mortari et al. ............................ 424/93.7

FOREIGN PATENT DOCUMENTS

| WO | 2004015091 | 2/2004 |
| WO | 2005017164 | 2/2005 |
| WO | 2005040391 | 5/2005 |
| WO | 2005052141 | 6/2005 |
| WO | 2005113748 | 12/2005 |

OTHER PUBLICATIONS

Sueblinvong et al (Translational Research, 156: 188-205, 2010)).*
Roper et al (Am J Physiol Lung Cell Mol Physiol 285: L691-L700, 2003).*
Brouwer et al (Am J Respir Crit Care Med vol. 187(5): 468-475, 2013).*
Portnoy et al., "Role of alveolar type II epithelial cells in pulmonary fibrosis" Lung Biology in Health and Disease (2004) 185 (Idiopathic Pulmonary) 573-608.
Bowden DH, Young L, Adamson IY "Fibroblast inhibition does not promote normal lung repair after hyperoxia". Exp Lung Res 1994; 20:251-262.
Richards RJ et al, 1987."Isolation, biochemical characterisation, and culture of lung type II cells of the rat". Lung 165: 143-158, 1987.
Johnson NF, et al., "Epithelial progenitor cells in the rat respiratory tract". Biology, toxicology, and carcinogenesis of respiratory epithelium. Thomassen, DG and Nettesheim, P(E.D). Hemipere publish Corporation, New York: 1990; 1-308.
Crapo et al., "Cell numbers and cell characteristics of the normal lung". Am. Rev. Respir. Dis. 126:332-337, 1982.
C. Fauli i Trillo, et al., "Tratado de Farmacia Galenica", 10th Ed., 1993, Luzan 5, S.A. de Ediciones.

* cited by examiner

*Primary Examiner* — Anoop Singh
*Assistant Examiner* — Magdalene Sgagias
(74) *Attorney, Agent, or Firm* — Sughrue Mion, PLLC

(57) ABSTRACT

It describes the use of type II pneumocytes as inhibitory agents of fibroblast proliferation, for which reason they can be used in the preparation of a drug for the treatment of lung diseases which present with pulmonary fibrosis.

7 Claims, 2 Drawing Sheets

METHOD FOR USING TYPE II PNEUMOCYTES IN PULMONARY FIBROSIS

CROSS-REFERENCE TO PRIOR APPLICATION

This application is a U.S. national phase application under 35 U.S.C. §371 of International Patent Application No. PCT/ES2006/070182 filed Nov. 27, 2006, which claims the benefit of priority to Spanish Patent Application No. P200502939 filed Nov. 28, 2005, the disclosures of all of which are hereby incorporated by reference in their entireties. The International Application was published in Spanish on May 31, 2007 as WO 2007/060278 A1.

FIELD OF THE INVENTION

The invention relates, in general, to the treatment of lung diseases which present with pulmonary fibrosis; and, in particular, with the use of type II pneumocytes in the treatment of said diseases.

BACKGROUND OF THE INVENTION

Among the lung diseases which present with pulmonary fibrosis we have diffuse interstitial lung diseases (DILD), which constitute a group of conditions with similar clinical, radiological and functional respiratory manifestations, wherein the main anatomopathological alterations affect the alveolar-interstitial structures. Furthermore, on many occasions, they also affect the small respiratory tracts, as well as the pulmonary vessels. This group of lung diseases is characterized by the inflammation and scarring of the alveoli and their support structures (the interstice), which leads to the loss of functional alveolar units and a reduction in the transfer of oxygen from the air to the blood.

The etiology of DILDs is very varied. At present, more than 150 different causes are known, although it is only possible to identify the causal agent thereof in approximately 35% of them. Their classification has been modified recently after the consensus prepared by the American Thoracic Society (ATS) and the European Respiratory Society (ERS) (see Table 1). Several groups of DILD are distinguished. The first group corresponds to idiopathic interstitial pneumonias, although this group also includes granulomatous lung diseases, such as sarcoidosis. In the second group appear the DILD of known cause or associated to other well-defined clinical entities; said group includes the pulmonary manifestations of collagen diseases, which frequently have a histology undistinguishable from idiopathic interstitial pneumonias, as well as the DILD caused by drugs, organic dust (extrinsic allergic alveolitis), inorganic dust (pneumoconiosis) and those associated to hereditary diseases. The third group is formed by a set of diseases which, although idiopathic, have well-defined symptoms and histology.

TABLE 1

| Classification of diffuse interstitial lung diseases (DILD) |
| --- |
| Idiopathic interstitial pneumonias |
| Idiopathic pulmonary fibrosis |
| Acute interstitial pneumonia |
| Non-specific interstitial pneumonia |
| Respiratory bronchitis with interstitial lung disease (respiratory bronchitis/DILD) |
| Desquamative interstitial pneumonia |
| Cryptogenetic organizing pneumonia |
| Lymphocytic interstitial pneumonia |
| Sarcoidosis of known or associated cause |
| Associated to collagen diseases |
| Caused by inorganic dust (pneumoconiosis) |
| Induced by drugs and radiotherapy |
| Caused by organic dust (extrinsic allergic alveolitis) |
| Associated to hereditary diseases (Hermansky-Pudlak syndrome, etc.) |
| Primary or associated to other not well-defined processes |
| Alveolar proteinosis |
| Alveolar microlithiasis |
| Lymphangioleiomyomatosis |
| Pulmonary eosinophilias |
| Histiocytosis X (granulomatosis of Langerhans cells) |
| Amyloidosis |

The most frequent DILDs are idiopathic pulmonary fibrosis and sarcoidosis, followed by extrinsic allergic alveolitis and those associated to collagen diseases.

Idiopathic pulmonary fibrosis (IPF) is the most frequent DILD and relates to pathologies which have a form of chronic interstitial fibrosing pneumopathy, limited to the lung and associated to a histopathological pattern of usual interstitial pneumonia (classic pattern associated to biopsy of the IPF). The estimated prevalence of the IPF is of 20 cases per each 100,000 (20/100,000) inhabitants in men and 13/100,000 in women. This disease may be presented at any age although it is most common between 40 and 70 years of age. Once the disease is diagnosed, the mortality is 50% after 5 years. The incidence, the prevalence and the mortality rate increases with age.

Its etiology is unknown and, within the iodiopathic interstitial pneumonias, it is that of worse prognosis. Most patients have the symptoms for many months (6-24 months) before being diagnosed. The first clinical manifestations include a progressive difficulty in breathing, dyspnea of effort, dry cough without apparent cause and crepitant sounds in the auscultation.

A large number of mechanisms have been proposed to explain the pathogeny of IPF. In general, it is considered that inflammatory cells act directly on the fibroblasts, through a large variety of inflammatory mediators, cytokines and growth factors, although an important role is also played by the interactions of these inflammatory modulators with the cells of the pulmonary parenchyma. As this pathological process takes place between the distal units of the lung (terminal bronchioles and alveoli), the interactions between the inflammatory cells with the epithelium and the pulmonary endothelium are also important. On the other hand, it should be highlighted that not only the inflammatory cells and the epithelials affect the fibroblasts, but they also alter the inflammatory and parenchymatic cells. In the normal lung, the interstice of the alveoli is very thin and the number of fibroblasts is limited. Most of the fibroblasts and collagen fibres are distributed throughout the vessels and the conducts of the air tracts. It seems that the balance between fibrotic and antifibrotic factors gives rise to the suppression of the proliferation of fibroblasts and the extracellular matrix.

Currently, it is considered that IPF is the end result of an unknown aggression which causes a chronic inflammation associated to the destructuring of the lung tissue and to the formation of fibrosis as a result of normal repair of the lesions. All of this would give rise to a progressive accumulation of extracellular matrix, a decrease between the fibroblast-myofibroblast balance, the continued death of epithelial cells and, finally, an abnormal re-epithelializing.

The fundamental objectives of the treatment for DILD consist, in general, of avoiding exposure to the causal agent, suppressing the inflammatory component of the disease (alveolitis) and treating the complications. The first objective can only be achieved in the diseases of known etiology. The suppression of alveolitis is the only therapeutic means in the DILDs of unknown cause, since there are no antifibrotic drugs with proven efficacy. The drugs used are glucocorticoids and immunodepressants. The indications and duration of the treatment vary according to the type of DILD. A recent study has demonstrated that sildenafil causes pulmonary vasodilation and improvement in gaseous exchange. However, there is no recommended strategy.

Although the pathogenic process suggests that there exist numerous theoretical points for different therapeutic interventions, the treatment has always been restricted, in practice, to therapies with antiflammatories and, recently, lung transplant. The different current treatments include corticosteroids (prednisone), immunosuppressants/cytotoxic agents (azathioprine, cyclofosfamide) and antifibrotic agents (colchicine or D-penicillamin) alone or in combination.

Unfortunately, none of the pharmacological therapies that have been tested have demonstrated to be useful for improving patients' prognosis.

Lung transplant is the last therapeutic option for DILDs which progress to fibrosis and cause respiratory insufficiency. There are more than 120 causes of DILD which evolve to fibrosis and, therefore, it is very difficult to identify the window of the transplant (suitable moment for the transplant in each patient, without it being too early or late that it compromises the viability of the transplant).

Currently, it is thought that the new therapies may include: oxidant agent inhibitors, cytokine inhibitors, protease inhibitors, fibroblast or growth factor inhibitors, antifibrotic drugs, modifications to the diet, better efficacy of the drugs administered via intrapulmonary route, such as the use of liposomes, antioxidants, leukocyte integrin inhibitors, and, finally, gene therapy.

Other agents with the capacity to block fibrogenesis can be used for the treatment of DILDs. Relaxin, a peptide which is used in the last phases of gestation and contributes to remodelling the pubic ligaments, decreases collagen production in fibroblast cultures and alters the balance between proteinases and anti-proteinases, in favour of the breaking of the matrix. Sumarin, a synthetic compound which has been used for many years to treat infections caused by nematodes, inhibits the effects of numerous profibrotic growth factors. Endothelin-1, a mitogenic and vasoactive peptide which is synthesized and segregates in the vascular endothelium and in the epithelium of the air tracts, has been found associated to the fibroblastic focus of biopsies and it can be obtained in the broncho-alveolar washes; in animal models, the inhibition of endothelin-1 avoids scarring after causing a pulmonary lesion. Angiotensin II is another peptide with mitogenic effects in the fibroblasts.

Since the epithelial lesion can also be produced, in part, by oxygen free radicals (OFR), it has been suggested that antioxidant strategies can be beneficial. Possible strategies will include the administration of antioxidant enzymes or promoting an increase in the gene expression thereof. The natural scavenger agent of the OFR suppresses the proliferation of pulmonary fibroblasts in response to mitogens. Taurine and niacin inhibit the development of fibrosis in animal models: the use of high doses of N-acetyl-L-cysteine, as glutation precursor, taurine and OFR scavenger agents, as therapeutic combination in immunosuppressant therapies for the FPL.

Another potential strategy for the treatment of said DILDs could be interference in the process of leukocyte recruitments. The adhesion molecules play a very important role in this process. Antibodies against these adhesion molecules have shown prevention in the deposition of collagens in animal models of pulmonary lesion.

Immunomodulating drugs have also been studied in both in vitro studies and in research animals. These works suggest that the modification of the inflammatory response in tissue repair may modulate the degree of final fibrosis after pulmonary lesion.

An effective therapy should try to prevent or inhibit the fibroproliferative response and be aimed at improving the repair of alveolar re-epitheliazing. In this way, the impact of the disease would be reduced, improving the patients' health. In other words, it would be suitable to induce the death of the fibroblasts, and not those of the epithelial cells, since this would give rise to good re-epitheliazing. However, some studies suggest that the inhibition of the fibroblast growth does not give rise to good re-epitheliazing [Bowden D H, Young L, Adamson I Y. Fibroblast inhibition does not promote normal lung repair after hyperoxia. Exp Lung Res 1994; 20:251-262].

Another therapeutic challenge is related to the possibility that the agents capable of directly inducing the proliferation of the type II epithelial cells decrease the fibrotic response to different aggressions and reduce cell death.

SUMMARY OF THE INVENTION

Now it has been found, surprisingly, that the transplant of type II pneumocytes to rats wherein pulmonary fibrosis has been induced with bleomycin (experimental model in idiopathic pulmonary fibrosis) reverses the fibrogenesis process and stops the progression of the disease. The Example which accompanies the present description reveals that, after the induction of pulmonary fibrosis in rats by the administration of bleomycin and the subsequent intratracheal transplant of murine type II pneumocytes, an inhibition of fibroblast proliferation is achieved as well as a recovery of the lung tissue in the transplanted rats. The tests developed by the inventors show that an increase in body weight is produced in the transplanted animals as well as a reduction in lung weight. Likewise, the inventors have observed that correct re-epitheliazing of the damaged lung is achieved by transplanting said cells. Therefore, the transplant of type II pneumocytes by intratracheal route produces a synergic defect in the transplanted animals since, on one side, it checks the growth of the fibroblasts, and, on the other side, it produces a correct re-epitheliazing of the damaged lung, thus detaining the progression of the disease. The treatment with said type II pneumocytes can be combined, if desired, with other therapies useful in the treatment of lung diseases which present with pulmonary fibrosis.

Therefore, the present invention relates to the use of type II pneumocytes in the preparation of a pharmaceutical composition for the treatment of lung diseases which present with pulmonary fibrosis. In a particular embodiment, said lung diseases are selected from DILDs, among those in which IPF is found, and some alterations of the immune system, among which we have sclerotic oedema.

DETAILED DESCRIPTION OF THE INVENTION

Figure 1:
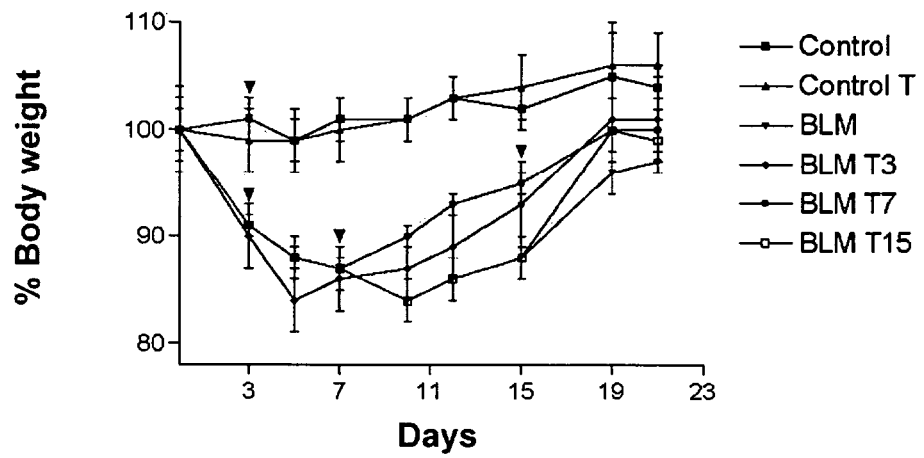
FIG. 1 is a graphic which represents the evolution of the animals' body weight; on day zero (0) the animals receive a treatment with bleomycin (BLM) which give rise to weight loss, the arrows show the days of the cells transplants (3, 7 and 15 days). The graphic shows that the administration of type II pneumocytes makes the recovery of body weight faster in all the transplanted animals. The data represent the mean±SEM of a total of 8 animals per group.

The present invention relates to the use of type II pneumocytes in the preparation of a pharmaceutical composition for the treatment of lung diseases which present with pulmonary fibrosis.

The term "type II pneumocytes" relates to pulmonary epithelial cells with a cuboidal appearance, whose apical surface is covered by microvilli and its cytoplasm is full of bodies of laminar inclusions composed of lipids and proteins which constitute the surfactant. An important function of type II pneumocytes (or type II epithelial cells) is the synthesis, storage and secretion of the pulmonary surfactant, which acts by reducing the surface tension and preventing the collapse of the alveoli. Type II epithelial cells comprise 14% of the total of the alveolar epithelial cells, these cells may be separated from other lung cells using conventional techniques [Richards R J et al, 1987. Isolation, biochemical characterisation, and culture of lung type II cells of the rat. Lung 165: 143-158]. Type II pneumocytes are the progenitors of type I pneumocytes [Johnson N F et al., 1990. Epithelial progenitor cells in the rat respiratory traxt. In: Biology, toxicology, and carcinogenesis of respiratory epithelium. Thomassen, D G and Nettesheim, P (E.d). Hemipere publish Corporation, New York: 1990; 1-308]. The term "type I pneumocytes" relates to epithelial lung cells specialized in gas exchange. Type I cells are very thin and flat and cover 95% of the alveolar surface [Crapo et al, 1982. Cell numbers and cell characteristics of the normal lung. Am. Rev. Respir. Dis. 126:332-337].

In normal conditions, approximately 1% of type II pneumocytes are responsible for the renewal of the alveolar surface being differentiated from type I pneumocytes This fact is important since type I pneumocytes are especially vulnerable to pulmonary lesion due to their surface and simplicity of their cytoplasm. In these circumstances, type II pneumocytes proliferate and repopulate the surface of the alveoli, providing the integrity of the epithelium. Thus, said type II pneumocytes come to be type I pneumocytes, completely restructuring the alveolar surface.

To put the invention into practice, the type II pneumocytes can be "wild type" (or "wt") type II pneumocytes, i.e. they have not been genetically manipulated. Alternatively, if desired, said type II pneumocytes can be genetically modified to increase, boost or favour the fibrogenesis inhibiting activity of said "wt" type II pneumocytes and/or to increase, boost or favour the re-epithelializing of said "wt" type II pneumocytes, giving rise to said "genetically modified type II pneumocytes" in this description. Illustrative, non-limitative, examples of modifications which can be introduced include modifications aimed at overexpressing proteins related to the production of pulmonary surfactant, for example, proteins A and D of the surfactant, etc., as well as modifications aimed at increasing the proliferation of type II pneumocytes, for example, keratinocyte growth factor, etc., among others. The genetic modifications to be carried out on the type II pneumocytes may be performed by conventional methods known by persons skilled in the art. Therefore, as used here, the term "type II pneumocytes" includes (i) "wt" type II pneumocytes, (ii) genetically modified type II pneumocytes, and (iii) combinations of "wt" type II pneumocytes and genetically modified type II pneumocytes.

The type II pneumocytes may be of autologous or heterologous origin, preferably the type II pneumocytes are of autologous origin.

The term "subject", as used here, relates to any member of an animal species of mammals and includes, but is not limited to, domestic animals, primates and humans; the subject is preferably a male or female human being of any age or race.

The term "lung diseases which present with pulmonary fibrosis" relates to lung diseases characterized by the presence of scars in the lungs so that, gradually, the air sacs (alveoli) are replaced by fibrotic tissue. Illustrative, non-limitative examples of said lung diseases which present with pulmonary fibrosis include diffuse interstitial lung diseases (DILD), as well as some alterations of the immune system (e.g. rheumatoid arthritis, sclerotic oedema, polymyositis, and, in rare cases, systemic lupus erythematosus). Other frequent causes of pulmonary fibrosis include (by way of non-limitative illustration): the infections caused by virus, rickettsias, mycoplasmas and disseminated tuberculosis; the inhalation of organic or inorganic dust, for example, mineral dust such as silica, carbon, etc., metal dusts and asbestos, etc.; the inhalation of gases, fumes and vapours (e.g. chlorine, sulphur dioxide, etc.); radiotherapy for antitumour treatments and industrial radiations; and the intake of some drugs and toxic substances such as bleomycin, methotrexate, bususlfan, cyclophosphamide, gold, penicillamine, nitrofurantoin, sulfonamides, amiodarone, paraquat, etc.; in general, these agents produce, in principle, diffuse diseases of the pulmonary parenchyma.

As has been previously described, the term "DILD" refers to lung diseases characterized by the inflammation and scarring (fibrosis) of the alveoli and their support structures (the interstice). Illustrative, non-limitative examples of said DILD include idiopathic interstitial pneumonias, granulomatous lung diseases and DILD of known cause or associated to other well-defined clinical entities. In a particular embodiment, said pulmonary pathology is selected from idiopathic pulmonary fibrosis (IPF), acute interstitial pneumonia, non-specific interstitial pneumonia, respiratory bronchitis with lung disease (respiratory bronchitis/DILD), desquamative interstitial pneumonia, cryptogenetic organizing pneumonia, lymphocytic interstitial pneumonia, sarcoidosis, DILD associated to collagen diseases, caused by inorganic dust (pneumoconiosis), induced by drugs and radiotherapy, caused by organic dust (extrinsic allergic alveolitis), associated to hereditary diseases, alveolar proteinosis, alveolar microlithiasis, lymphangioleiomyomatosis, pulmonary eosinophilias, histiocytosis X (granulomatosis of Langerhans cells), amyloidosis. In a particular embodiment, said DILD is FPI.

In another particular embodiment, said lung disease which presents with pulmonary fibrosis is an alteration of the immune system, for example, rheumatoid arthritis, sclerotic oedema, polymyositis, and, in rare cases, systemic lupus erythematosus. The term "sclerotic oedema", as used here, refers to a rare disease of the connective tissue which may cause the thickening and hardening of the skin tissues, joints and internal organs such as the lungs. This form is more serious and can be fatal.

For its administration in the treatment of a pulmonary pathology which presents with pulmonary fibrosis, type II pneumocytes shall be formulated in a suitable pharmaceutical composition, hereinafter called "pharmaceutical composition of the invention", in a therapeutically effective quantity, together with one or more vehicles, adjuvants or pharmaceutically effective excipients.

As has previously been mentioned, the term "type II pneumocytes" includes "wt" type II pneumocytes, genetically modified type II pneumocytes, and combinations of "wt" type II pneumocytes and genetically modified type II pneumocytes. Therefore, in a particular embodiment, the pharmaceutical composition of the invention comprises "wt" type II pneumocytes. In another particular embodiment, the pharmaceutical composition of the invention comprises genetically modified type II pneumocytes. In another particular embodiment, the pharmaceutical composition of the invention comprises a mixture or combination of "wt" type II pneumocytes and genetically modified type II pneumocytes.

In the sense used in this description, the expression "therapeutically effective quantity" refers to the quantity of type II pneumocytes ("wt" and/or genetically modified) contained in the pharmaceutical composition of the invention calculated to produce the desired effect and, in general, will be determined, among other causes, by the characteristics typical of said type II pneumocytes and the effect of inhibition of the proliferation of fibroblasts and re-epitheliazing of the alveolar surface to be achieved. In general, the therapeutically effective quantity of type II pneumocytes to be administered will depend, among other factors, on the subject that is going to be treated, the pathology they suffer from, its severity, the chosen form of administration, etc. For this motive, the doses mentioned in this invention must be considered only as guides for the person skilled in the art, and they should adjust the dose in accordance with the aforementioned variables. By way of non-limitative illustration, the pharmaceutical composition of the invention can be administered in a single dose containing between approximately $1 \times 10^6$ cells and approximately $25 \times 10^6$ cells, advantageously between approximately $2.5 \times 10^6$ cells and approximately $20 \times 10^6$ cells, preferably, between approximately $5 \times 10^6$ cells and approximately $10 \times 10^6$ cells, depending on the aforementioned factors. The dose of type II pneumocytes can be repeated, depending on the condition of the patient and his or her evolution, on time intervals (days, weeks or months) which will have to be established in each case by the specialist.

The pharmaceutical composition of the invention will be prepared, in general, in a suitable pharmaceutical form of administration to facilitate contact between the type II pneumocytes ("wt" and/or genetically modified) and the lung tissue affected in order that the desired effect is produced, i.e. an inhibition of the proliferation of fibroblasts and, advantageously, a correct re-epitheliazing of the affected tissue; for this reason, said pharmaceutical composition of the invention shall be formulated in a suitable pharmaceutical form for the chosen administration route. Said pharmaceutical composition of the invention can be administered in vivo directly on the lung tissue of the subject in need of treatment, or be administered in vitro on the previously affected tissue later re-implanted in the subject in need of treatment after administration of the pharmaceutical composition of the invention.

For its administration in vivo to a subject in need of treatment, the pharmaceutical composition of the invention can be administered by any appropriate route, such as, for example by pulmonary, intratracheal, nasal, parenteral, intraperitoneal route, etc., preferably, by pulmonary, intratracheal, nasal or parenteral route, for which reason the pharmaceutical composition of the invention shall incorporate the suitable pharmaceutically acceptable vehicles, excipients and auxiliary substances in accordance with the selected pharmaceutical form of administration. Said pharmaceutical forms of administration can be prepared by conventional methods. A review of the different pharmaceutical forms of administration of drugs and of their preparation can be found in the book "Tratado de Farmacia Galénica", by C. Faulí i Trillo, $10^{th}$ edition, 1993, Luzán 5, S.A. de Ediciones. In any case, the pharmaceutical composition of the invention can be administered using the suitable equipment, apparatus and devices, which are known by persons skilled in the art, for example catheters, cannulas, etc.

On the other hand, for the in vitro administration of the pharmaceutical composition of the invention it is possible to proceed as indicated below. In the first place, the lung tissue which is damaged or affected by fibrosis is removed (e.g. a lung lobe). Next, the lung tissue is put in contact with the pharmaceutical composition of the invention under conditions which permit the contact and adhesion of type II pneumocytes to the lung tissue so that said cells can exert their inhibitory action of the proliferation of fibroblasts and, advantageously, re-epithelializing of the affected tissue. Finally, the treated lung tissue is implanted in the subject. Both the removal of the lung tissue and its implantation in the subject once subjected to treatment with the pharmaceutical composition of the invention can be carried out using conventional methods, typically by surgical methods known by persons skilled in the art. The pharmaceutical composition of the invention can be placed in contact with the lung tissue using conventional methods, for example, by injection of the pharmaceutical composition of the invention in the lung tissue, or by washing the lung tissue with the pharmaceutical composition of the invention, or immersing the lung tissue in a bath which contains the pharmaceutical composition of the invention, or by "seeding" the type II pneumocytes directly on the lung tissue in order to establish a cell population, etc. The lung tissue extracted from the subject can be re-implanted in the subject, once treated with type II pneumocytes, after a variable period of time, typically between 6 and 24 hours after its extraction so as not to compromise the viability of the lung tissue.

In either case (in vivo or in vitro administration), the pharmaceutical composition of the invention shall be administered using the suitable equipment, apparatus and devices which are known by persons skilled in the art, for example, catheters, cannulas, etc.

In a particular embodiment, the pharmaceutical composition of the invention is prepared in the form of an aqueous suspension or solution, in a pharmaceutically acceptable vehicle, such as a saline solution, a phosphate buffered saline solution (PBS), or any other pharmaceutically acceptable vehicle. Illustrative, non-limitative examples of the pharmaceutically acceptable vehicles for the administration of type II pneumocytes include, for example, a sterile saline solution (e.g. 0.9% NaCl). The pharmaceutical composition of the invention can also contain, if necessary, other auxiliary substances or pharmaceutically acceptable compounds, such as co-solvents, additives to stabilize the suspension, e.g. pharmaceutically acceptable preservatives, acids, bases or buffers which are pharmaceutically acceptable to adjust the pH, surfactants, etc. Likewise, to stabilize the suspension, it is possible to add metal chelating agents. The stability of the cells present in the liquid medium of the pharmaceutical composition of the invention can be increased by the addition of additional substances, for example, amino acids, such as aspartic acid, glutamic acid, etc. These pharmaceutically acceptable substances which can be used in the pharmaceutical composition of the invention are known, in general, by persons skilled in the art and are typically used for the preparation of formulations for cell compositions. Additional information on these substances can be found in treatises of galenic or animal health, for example, in the book "Tratado de Farmacia Galénica", by C. Faulí i Trillo, 10$^{th}$ edition, 1993, Luzán 5, S.A. de Ediciones.

The pharmaceutical composition of the invention can be conserved until its use by conventional methods known by persons skilled in the art; in a particular embodiment, the pharmaceutical composition of the invention can be stored until its use by freezing.

The pharmaceutical composition of the invention can be used together with other additional drugs used in the prevention and/or treatment of said pulmonary pathologies which present with pulmonary fibrosis in active form to provide a combination treatment. Said additional drugs can form part of the same pharmaceutical composition provided by this invention or, alternatively, they can be provided in the form of a separate composition for its simultaneous or sequential administration to those of the pharmaceutical composition of the invention.

Illustrative, non-limitative examples of additional drugs which can be used to provide a combination therapy include anti-inflammatories, antifibrotics, growth factors of type II pneumocytes such as keratinocyte growth factor, etc.; fibroblast growth factor inhibitors such as antagonists of transforming growth factor β (TGFβ), etc.; angiotensin II inhibitors, such as sartans, e.g. losartan, etc.

As previously mentioned, the pharmaceutical composition of the invention can be administered in vitro, i.e. on the lung tissue damaged or affected by fibrosis previously extracted from the subject in need of treatment in order to inhibit the proliferation of fibroblasts and, advantageously, re-epithelialize the affected lung tissue. Therefore, in another aspect, the invention relates to a method to inhibit in vitro the proliferation of fibroblasts or to re-epithelialize lung tissue which comprises placing lung tissue in contact with a pharmaceutical composition of the invention. In a particular embodiment, said lung tissue is damaged lung tissue, i.e. affected by pulmonary fibrosis, and which has been previously extracted from a subject who suffers from lung disease which presents with pulmonary fibrosis. As previously mentioned, the extraction of the lung tissue can be carried out by conventional methods, typically surgical, known by persons skilled in the art. The pharmaceutical composition of the invention can be placed in contact with the lung tissue by conventional methods, for example, by injection of the pharmaceutical composition of the invention in the lung tissue, or by washing the lung tissue with the pharmaceutical composition of the invention, or by immersing the lung tissue in a bath which contains the pharmaceutical composition of the invention, or by "seeding" the type II pneumocytes directly on the lung tissue in order to establish a cell population, etc. The lung tissue extracted from the subject and subjected to treatment with type II pneumocytes, if desired, can be re-implanted in the subject, after a variable period of time, typically between 6 and 24 hours after its extraction.

In another aspect, the invention is related to a method for the treatment of a lung disease which presents with pulmonary fibrosis in a subject in need of treatment which comprises administering a pharmaceutical composition which comprises type II pneumocytes to said subject. The administration of the pharmaceutical composition of the invention can be carried out using conventional methods as previously mentioned in relation to the in vivo administration of said pharmaceutical composition of the invention to a subject in need of treatment.

In another aspect, the invention relates to a method for the treatment of a lung disease which presents with pulmonary fibrosis in a subject in need of treatment which comprises extracting lung tissue from said subject, placing it in contact with a pharmaceutical composition which comprises type II pneumocytes, and re-implanting it in said subject. In a particular embodiment, said lung tissue is damaged lung tissue, i.e. affected by pulmonary fibrosis, and has previously been extracted from a subject who suffers from lung disease which presents with pulmonary fibrosis. In this case, the pharmaceutical composition of the invention can be placed in contact with the lung tissue extracted by conventional methods as previously mentioned, for example, by injection of the pharmaceutical composition of the invention in the lung tissue, or by washing the lung tissue with the pharmaceutical composition of the invention, or by immersing the lung tissue in a bath which contains the pharmaceutical composition of the invention, or by "seeding" the type II pneumocytes directly on the lung tissue in order to establish a cell population, etc. The lung tissue extracted from the subject can be re-implanted in the subject, once treated, with type II pneumocytes, after a variable period of time, typically between 6 and 24 hours after its extraction.

The following example illustrates the invention and should not be considered limitative of the scope thereof.

Example 1

Transplant of Type II Pneumocytes in Rats Wherein Pulmonary Fibrosis has been Induced I. Materials and Methods Female and male rates of the Lewis strain were used (Harlan Inerfauna, Barcelona) of body weight between 175-200 grams at the start of the experiments.

The animals were housed in constant environmental conditions of temperature 22-24° C., relative humidity 60-65% and with light/darkness cycles of 12 hours. They were given a standard diet of AO4 food (Panlab, Barcelona) and water from the Barcelona network ad libitum. All the studies were carried out in accordance with the regulatory rules of the European Union for animal experimental models (Directive 86/609/EEC).

1.1 Experimental Model

Pulmonary fibrosis was caused by an intratracheal instillation of single dose of 0.25 U of bleomycin per 100 grams of animal weight, dissolved in a volume of 0.25 ml of saline solution (0.9% NaCl). The control animals received the same volume of saline solution instead of bleomycin. The intratracheal instillation is performed with the animals anaesthetised with halothane by inhalatory route.

The transplants of type II pneumocytes were performed in female Lewis rats 3, 7 and 15 days after the induction of the pulmonary fibrosis. Said transplants were carried out by intratracheal instillation of the cells ($2.5 \times 10^6$ cells per animal, suspended in 0.5 ml of saline solution) under inhalatory anaesthesia with halothane. A transplant was carried out on the control animals by intratracheal instillation of the cells ($2.5 \times 10^6$ cells per animal/suspended in 0.5 ml of saline solution) under inhalatory anaesthesia with halothane, 3 days after the instillation of saline solution. All the animals were sacrificed 21 days after the induction of the pulmonary fibrosis. The animals were sacrificed by a lethal injection by intraperitoneal route of sodium pentobarbital (100 mg/kg) and later exsanguinations of the animal by the abdominal aorta; finally, the lungs joined to the trachea were extracted.

1.2 Preparation of the Cells

Type II epithelial cells (pneumocytes) were isolated from male Lewis rats. Firstly, the animals were anaesthetised with sodium pentobarbital (100 mg/kg). The lungs were perfused with saline solution by cannulation of the pulmonary artery. The lungs were extracted and a broncho-alveolar wash was carried out (4×10 ml) to eliminate the alveolar macrophages. After digestion with trypsin (Sigma) in a water bath at 37° C., the lungs were cut into small fragments and 5 ml of bovine foetal serum and DNase were added (Roche Diagnostics) until taking the solution to a final volume of 20 ml. The cell suspension was first filtered through a gauze fabric, a 50 µm filter and finally through a 30 µm filter. The cells were separated by a percol gradient (Amersham biosciences) and centrifuging at 250 g, for 20 minutes at 10° C. The band of cells was collected which remained between the two gradients and DNase was added to a final volume of 40 ml. It was centrifuged at 250 g for 20 minutes at 10° C. The cell precipitate was resuspended with 5 ml of DCCM1 culture medium (Biological Industries) supplemented with 2 mM glutamine, 100 µg/ml of penicillin and 60 µg/ml of gentamicin. It was incubated for 1 hour to eliminate alveolar macrophages. After one hour, the cell suspension was centrifuged at 250 g for 20 minutes at 10° C. and they were washed twice using centrifugation in saline solution. Finally, they were resuspended in saline solution (0.5 ml/$2.5 \times 10^6$ cells).

The viability and the cell count was facilitated by staining with Trypan blue (Sigma). Each animal received an average of approximately $2.5 \times 10^6$ type II pneumocytes resuspended in sterile physiological serum.

1.3 Statistical Analysis

All the results relate to the mean±SEM. The significant differences between means were determined using an ANOVA variance analysis and a Neuman Keuls post test. A value of $p<0.05$ was considered statistically significant.

II. Results

In all the cases, the transplants of type II pneumocytes (T) were carried out several times after the induction of pulmonary fibrosis: day 3 (BLM T3), day 7 (BLM T7) and day 15 (BLMT15).

2.1 Measurement of Body Weight

Pulmonary fibrosis entails a loss of body weight. However, the results show that said loss is recovered before in the transplanted animals with type II pneumocytes (FIG. 1).

2.2 Measurement of the Lung Weight

Figure 2:
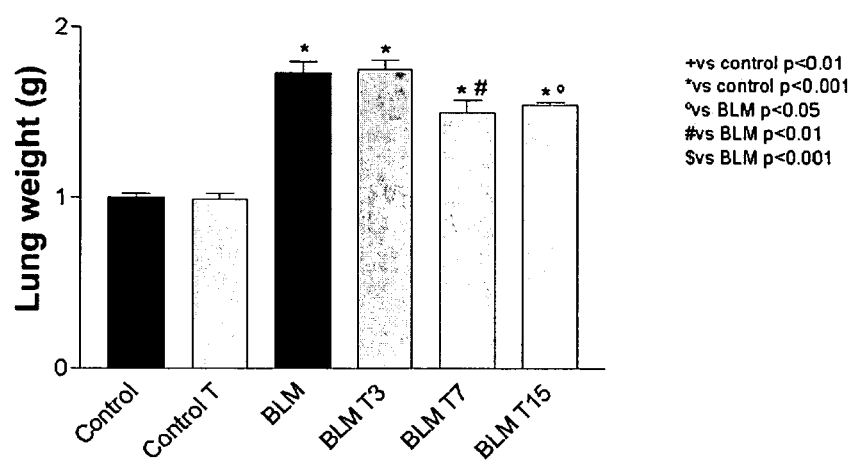
FIG. 2 is a bar diagram which represents the weight of the lungs in the control animals and in which pulmonary fibrosis (BLM) has been induced and the different times at which the cell transplants have been made (3, 7 and 15 days—BLM T3, BLM T7 and BLM TI5, respectively). The graphic shows that the administration of type II pneumocytes gives rise to a significant decrease in pulmonary weight in the transplanted animals after 7 days and after 15 days. The data represent the mean±SEM of a total of 8 animals per group.

Likewise, the weight of the lung, which significantly increases with the induction of pulmonary fibrosis, suffered a smaller increase in the groups of transplanted animals after 7 and 15 days with type II pneumocytes (FIG. 2).

2.3 Hydroxyproline Levels

Figure 3:
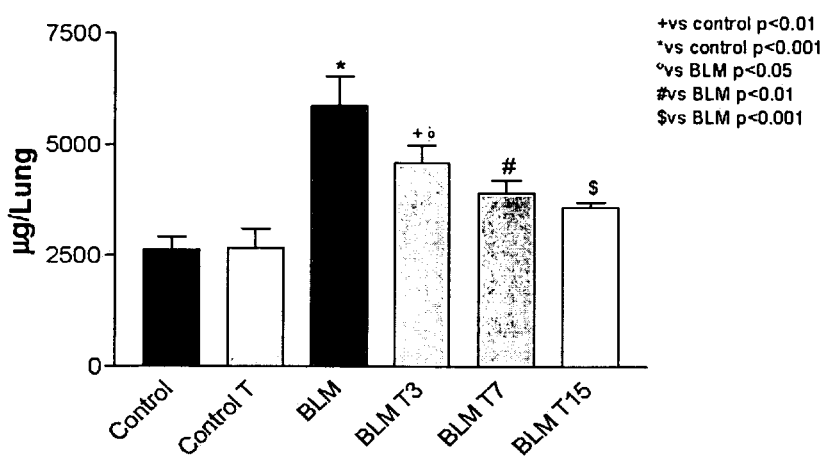
FIG. 3 is bar diagram which shows the hydroxyproline levels in the lung. The graphic reveals that the hydroxyproline levels in the lungs in which type II pneumocytes have been transplanted is reduced at all times (days 3, 7 and 15) with respect to the non-transplanted animals. This decrease in collagen levels is really evident in the transplanted animals after 7 and 15 days, where it is observed that the hydroxyproline levels are equal to the control animals. The data represent the mean±SEM of a total of 8 animals per group.
Figure 4:
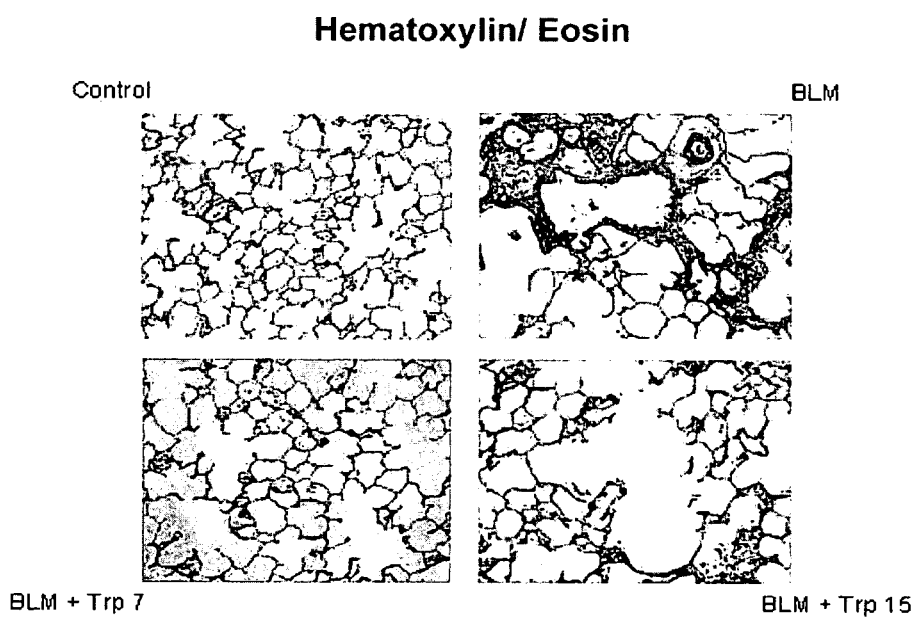
FIG. 4 shows optical microscope photographs of lung preparations. The photographs show a reduction in the foci of pulmonary fibrosis induced in those animals which have been transplanted with type II pneumocytes at different times (days 3, 7 and 15).

Finally, the determination of the hydroxyproline levels (specific marker of collagen deposition) showed significantly lower values in all the transplanted groups (FIG. 3). This result showed a very important reduction in the process of fibrosis in the pulmonary parenchyma. This reduction in the fibrotic process can also be observed in histological lung preparations (FIG. 4) of the treated animals.

The invention claimed is:

1. A method of reducing collagen deposition induced by pulmonary fibrosis comprising:
   intratracheally administering a pharmaceutical composition comprising autologous or allogeneic type II pneumocytes to a subject in need of treatment, and
   reducing collagen deposition induced by pulmonary fibrosis,
   wherein the type II pneumocytes have the following characteristics:
   1) the presence of bodies of laminar inclusions which constitute pulmonary surfactant, apical microvilli, cell-cell junctions and a cuboidal shape,
   2) can differentiate into type I pneumocytes, and
   3) can synthesize, store and secrete pulmonary surfactant.

2. The method according to claim 1, wherein said pulmonary fibrosis is a symptom of a diffuse interstitial lung disease (DILD).

3. The method according to claim 2, wherein said DILD is selected from idiopathic pulmonary fibrosis, acute interstitial pneumonia, non-specific interstitial pneumonia, respiratory bronchitis with interstitial lung disease (respiratory bronchitis/DILD), desquamative interstitial pneumonia, cryptogenetic organizing pneumonia, lymphocytic interstitial pneumonia, sarcoidosis, DLD associated to collagen diseases, caused by inorganic dust (pneumoconiosis), induced by drugs and radiotherapy, caused by organic dust (extrinsic allergic alveolitis), associated to hereditary diseases, alveolar proteinosis, alveolar microlithiasis, lymphangioleiomyomatosis, pulmonary eosinophilias, histiocytosis X (granulomatosis of Langerhans cells) and amyloidosis.

4. The method according to claim 1, further comprising reducing the number of fibrotic foci induced by the pulmonary fibrosis.

5. The method according to claim 4, wherein said subject is a human being.

6. The method according to claim 4, wherein said subject is a non-human mammal.

7. The method according to claim 1, wherein the type II pneumocytes are isolated from a lung tissue.

* * * * *